(12) United States Patent
Bramwell et al.

(10) Patent No.: US 9,675,792 B2
(45) Date of Patent: Jun. 13, 2017

(54) HEMOSTASIS MECHANISM AND METHOD

(71) Applicant: Cook Medical Technologies, LLC, Bloomington, IN (US)

(72) Inventors: Orville Bramwell, Bloomington, IN (US); Shavonna Warren, Bloomington, IN (US); Patrick Girard McElhaney, Jr., Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 242 days.

(21) Appl. No.: 14/287,804

(22) Filed: May 27, 2014

(65) Prior Publication Data

US 2015/0038919 A1 Feb. 5, 2015

Related U.S. Application Data

(60) Provisional application No. 61/862,198, filed on Aug. 5, 2013.

(51) Int. Cl.
*A61M 5/00* (2006.01)
*A61M 39/06* (2006.01)

(52) U.S. Cl.
CPC ... *A61M 39/0606* (2013.01); *A61M 2039/064* (2013.01); *A61M 2039/066* (2013.01); *A61M 2039/0626* (2013.01); *A61M 2039/0686* (2013.01); *A61M 2210/12* (2013.01)

(58) Field of Classification Search
CPC .............. A61M 39/06; A61M 39/0613; A61M 2039/062; A61M 2039/0626; A61M 2039/064; A61M 2039/066; A61M 2039/0673; A61M 2039/0686
See application file for complete search history.

(56) References Cited

U.S. PATENT DOCUMENTS

| 4,886,507 | A | | 12/1989 | Patton et al. | |
|---|---|---|---|---|---|
| 5,267,966 | A | * | 12/1993 | Paul | A61M 39/0606 137/845 |
| 5,324,271 | A | * | 6/1994 | Abiuso | A61M 39/0613 604/167.03 |
| 5,514,109 | A | | 5/1996 | Mollenauer et al. | |

(Continued)

FOREIGN PATENT DOCUMENTS

| WO | WO2012/175699 | * 12/2012 | ............ A61M 39/06 |
|---|---|---|---|

OTHER PUBLICATIONS

MeritMedical, Merit Hemostasis Valves and Angioplasty Accessories, catalog, Publication date: Aug. 4, 2013 or before, 4 pages, Merit Medical Systems, Inc., South Jordan, United States.

*Primary Examiner* — Emily Schmidt
(74) *Attorney, Agent, or Firm* — Liell & McNeil

(57) ABSTRACT

A hemostasis mechanism includes a housing having a valve body, a connector coupled to a distal end of the valve body, and a cap coupled to a proximal end of the valve body. A first valve is within the housing and has a fixed state of axial compression between the valve body and the cap. A second valve is within the housing and has a range of states of axial compression between the valve body and the connector. The first valve has a self-closing bias and forms a lower pressure seal about a medical device pushed therethrough. The second valve has a self-opening bias and forms a higher pressure seal about the medical device via adjustment of its state of axial compression.

18 Claims, 3 Drawing Sheets

(56) References Cited

U.S. PATENT DOCUMENTS

| | | |
|---|---|---|
| 5,895,376 A | 4/1999 | Schwartz et al. |
| 6,221,057 B1 | 4/2001 | Schwartz et al. |
| 6,458,103 B1 | 10/2002 | Albert et al. |
| 7,938,809 B2 | 5/2011 | Lampropoulos et al. |
| 7,981,090 B2 | 7/2011 | Plishka et al. |
| 8,070,731 B2 | 12/2011 | Wenchell et al. |
| 2014/0207083 A1* | 7/2014 | Pessin ............... A61M 39/0606 604/256 |

* cited by examiner

HEMOSTASIS MECHANISM AND METHOD

TECHNICAL FIELD

The present disclosure relates generally to hemostasis mechanisms and techniques used in performing transluminal procedures on a patient, and relates more particularly to a dual valve hemostasis mechanism forming lower and higher pressure seals about a medical device.

BACKGROUND

A wide variety of different sealing mechanisms are used to limit backflow of blood or other fluids from a patient during certain treatments or diagnostic procedures. In a typical scenario, a clinician controls such a mechanism to alternately block or open a conduit extending from outside the patient into an intraluminal space such as a vein or artery. Other mechanisms include a self-sealing valve through which a medical device is passed, automatically forming a seal. Transluminal devices such as wire guides and catheters may be passed through such a conduit when open, and backflow of blood or another fluid can be prevented when the conduit is closed. Since it is often necessary for transluminal devices to reside within the fluid conduit when a seal is established, many such mechanisms are engineered to fluidly seal around a wire guide, catheter, or the like.

One known manually operable design employs a push/pull sleeve or tube, which can be advanced through the center of a resilient gasket or the like positioned in the housing to open the gasket and provide a passage for introducing a medical device into the patient. Other manually operable designs employ a rotating mechanism which adjusts a different type of gasket between an open configuration and closed configuration, also sealing about a medical device. Known strategies of these general types have various drawbacks.

U.S. Pat. No. 5,514,109 to Mollenauer et al. is directed to an adjustable valve having a radially compressible sealing body. Mollenauer et al. teach an adjustable surgical valve having a sealing body with an axial passage extending through it, a toroidal body axially aligned with the sealing body, and a device that selectively changes the relative axial positions of the sealing body and the toroidal body. Mating surfaces of the sealing body and the toroidal body radially compress the axial passage of the sealing body when relative axial positions of the sealing body and the toroidal body are changed. This apparently causes the axial passage to seal with an instrument inserted through it, or seal with itself. The design set forth in Mollenauer et al. may have achieved its stated purposes, but appears relatively complex and likely expensive to manufacture.

SUMMARY OF THE DISCLOSURE

In one aspect, a hemostasis mechanism includes a housing having a valve body defining a longitudinal axis extending between a proximal body end and a distal body end, and including a cap coupled to the proximal body end and having a fixed axial location relative the valve body. The housing further includes a connector coupled to the distal body end and having an adjustable axial location relative the valve body, and a device passage formed in part in each of the valve body, cap, and connector. The hemostasis mechanism further includes a first valve positioned at least partially within the device passage and having a fixed state of axial compression between the valve body and the cap. The first valve has a first opening formed therein and a self-closing bias such that the first opening is normally closed. The first valve further forms a lower pressure seal about a medical device in response to pushing the medical device through the first opening in opposition to the self closing bias. The hemostasis mechanism further includes a second valve positioned at least partially within the device passage and having a range of states of axial compression between the valve body and the connector. The second valve has a second opening formed therein and a self-opening bias such that the second opening is normally open. The second valve further forms a higher pressure seal about the medical device via an adjustment of the state of axial compression in response to changing the axial location of the connector in opposition to the self-opening bias.

In another aspect, a method of limiting backflow of fluid during percutaneous transluminal treatment of a patient includes pushing a medical device for introducing into the patient through a normally closed opening in a first valve having a fixed state of axial compression between a valve body and a cap in a hemostasis mechanism, and forming a lower pressure seal about the medical device via a self-closing bias of the first valve. The method further includes advancing the medical device through a normally open opening in a second valve having a range of states of axial compression between the valve body and a connector in the hemostasis mechanism, and increasing the state of axial compression of the second valve in opposition to a self-opening bias thereof. The method further includes forming a higher pressure seal about the medical device via deformation of the second valve induced by the increase in the state of axial compression, and blocking backflow of fluid through the hemostasis mechanism via at least one of the higher pressure and lower pressure seals.

DETAILED DESCRIPTION

Figure 1:
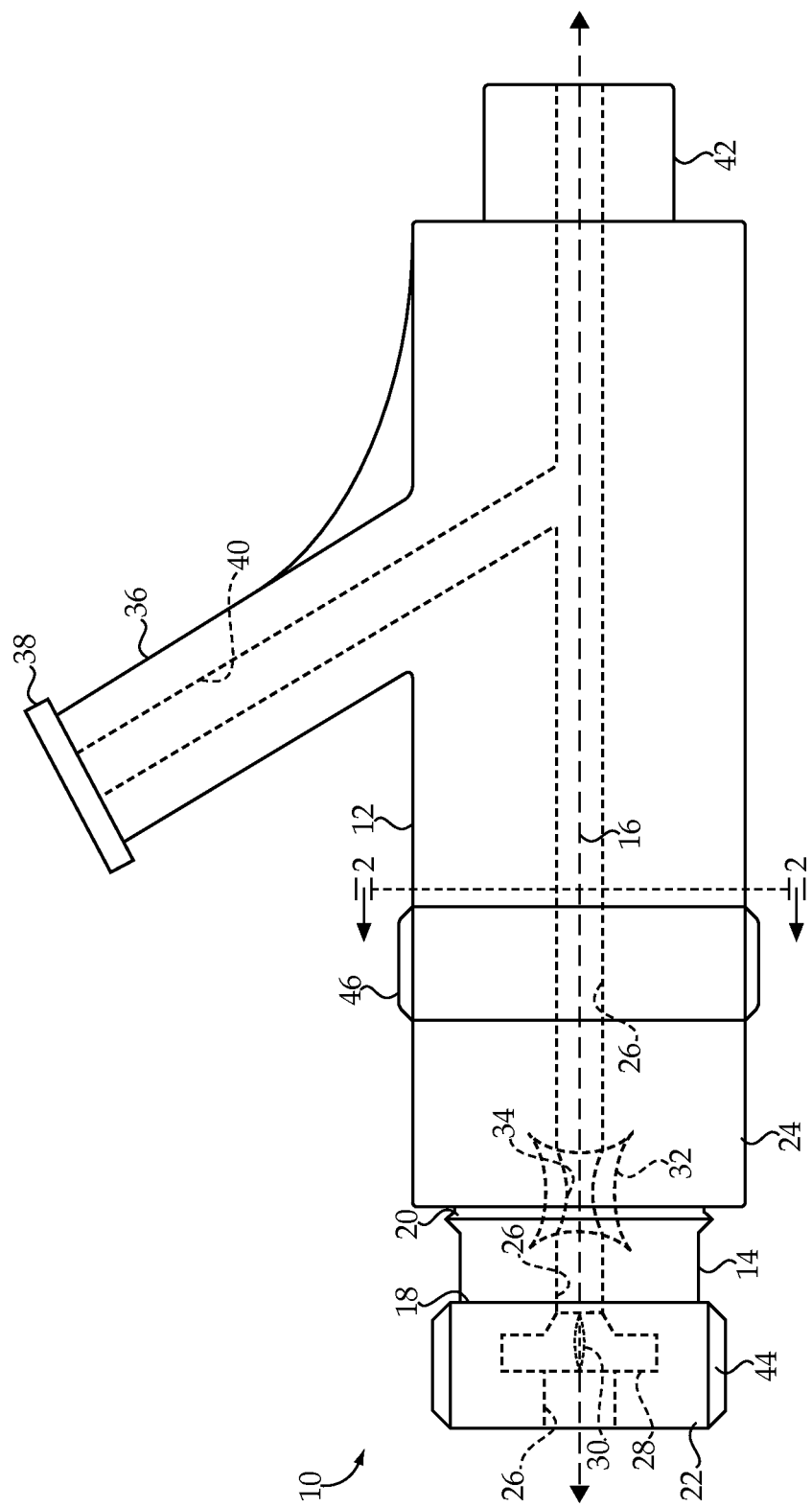
FIG. 1 is a side diagrammatic view of a hemostasis mechanism, according to one embodiment.

Referring to FIG. 1, there is shown a hemostasis mechanism 10 according to one embodiment and including a housing 12 having a valve body 14 defining a longitudinal axis 16 extending between a proximal body end 18 and a distal body end 20. Housing 12 further includes a cap 22 coupled to the proximal body end and having a fixed axial location relative valve body 14. Housing 12 further includes a connector 24 coupled to distal body end 20 and having an adjustable axial location relative valve body 14. A device passage 26 is formed in part in each of valve body 14, cap 22, and connector 24. Housing 12 may further include a side arm 36 having formed therein a side passage 40 in fluid communication with device passage 26. A fitting 42, which might be a luer fitting or the like, is located on side arm 36, and another fitting 42 which might also be a luer fitting, is located on or part of housing 12. Hemostasis mechanism 10 is applicable in the context of limiting backflow of fluid during percutaneous transluminal treatment of a patient according to a wide variety of procedures. As will be further apparent from the following description, mechanism 10 may be used to selectively provide a higher pressure seal to limit backflow of fluid through passage 26, for any procedure but especially procedures in which fluid is injected into the body of the patient such as through side passage 40. Mechanism 10 is also configured to provide a lower pressure seal without requiring any action on the part of a treating clinician. In connection with these and other applications contemplated herein, mechanism 10 can be expected to provide a simple, straightforward and effective means for limiting backflow of fluids such as injected saline, contrast agent or infusate, as well as body fluids such as blood.

To this end, mechanism 10 includes a first valve 28 positioned at least partially within passage 26 and having a fixed state of axial compression between valve body 14 and cap 22. The fixed state of axial compression means that once first valve 28 is positioned for service in assembled housing 12 no manipulation of mechanism 10 within the scope of its expected use will substantially change the forces first valve 28 is subjected to within housing 12 in an axial direction, at least relative to another valve discussed below. First valve 28 further has a first opening 30 formed therein, and has a self-closing bias such that first opening 30 is normally closed. In other words, when no external force is being applied to first valve 28, opening 30 will tend to be shut, fluidly sealing passage 26 via the tendency of first valve 28 to seal itself or seal about a medical device passed through device passage 26, as further discussed herein.

Mechanism 10 further includes a second valve 32 positioned at least partially within device passage 26 and having a range of states of axial compression between valve body 14 and connector 24. In contrast to the above description of first valve 28, manipulation of mechanism 10 by a clinician can be expected to change the extent to which second valve 32 is subjected to compressive forces in an axial direction, the significance of which will be further apparent from the following description. Second valve 32 has a second opening 34 formed therein, and a self-opening bias such that second opening 34 is normally open. A shape of valve 32 may be generally tubular, and in one embodiment valve 32 is a section of so-called Tuoy tubing. Again in contrast to first valve 28, when no forces external to second valve 32 itself are being applied, second opening 34 will have a tendency to remain open, providing fluid communications through device passage 26. Second valve 32 further forms a higher pressure seal about a medical device passed through passage 26 via an adjustment of the state of axial compression in response to changing the axial location of connector 24 in opposition to the self-opening bias. As noted, second valve 32 has a range of states of axial compression between valve body 14 and connector 24. The range of states of axial compression may impart a range of lower to higher pressure seals that can be obtained with second valve 32. As used herein, the terms lower pressure seal and higher pressure seal should be understood in contrast to one another. Moreover, the term lower should be understood to mean that the associated fluid seal can be overcome or fail in response to a relatively lower fluid pressure. In contrast, the higher pressure seal will tend to fail only if subjected to a relatively higher fluid pressure. Given the range of states of axial compression of second valve 32, it can be expected that second valve 32 could also form an even lower pressure seal than the seal formed by first valve 28, but be adjustable in a continuum to a state of axial compression forming a higher pressure seal than the seal formed by first valve 28. Example applications and the advantages associated with the formation of the lower pressure seal with first valve 28, and selective formation of higher pressure seals with second valve 32 will be further apparent from the following description.

To enable manipulation of mechanism 10 to form the higher pressure seal via second valve 32, the axial location of connector 24 relative valve body 14 can be adjusted by rotating the respective components relative to one another. To this end, cap 22 may be rotationally fixed to valve body 14, and connector 24 may be rotatable relative valve body 14. Cap 44 may be provided with a gripping feature 44 such as faces of a hex shape, and connector 24 may be equipped with the same or an analogous gripping feature 46. Knurls, a clover shape, or any other suitable gripping features might be used. Connector 24 is shown coupled with other parts of housing 12 that include side arm 36 and fittings 38 and 42. This configuration will be recognized by those skilled in the art as a typical Y-configuration. In other embodiments, connector 24 might be directly or indirectly coupled with any of a variety of different parts or devices, including catheters, sheaths, and all manner of typically tubular components or body pieces thereof.

Figure 2:
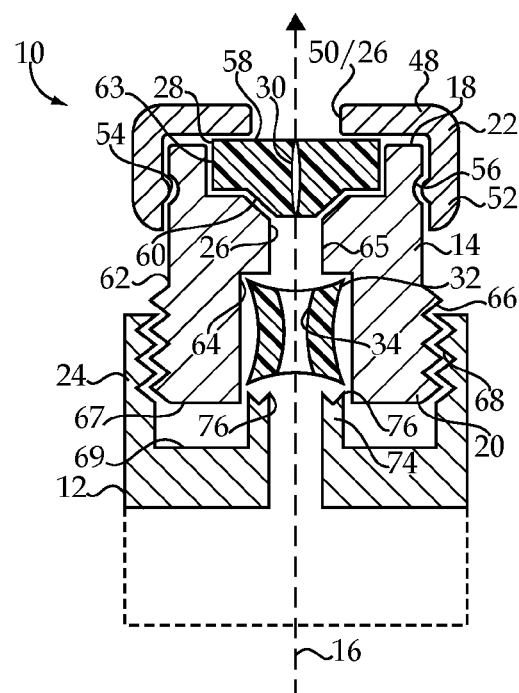
FIG. 2 is a sectioned view of a part of the hemostasis mechanism of FIG. 1, taken along line 2-2.

Referring also now to FIG. 2, there is shown a sectioned view taken along line 2-2 of FIG. 1. From FIG. 2 it may be noted that cap 22 has a radial part 48, and an axial part 52. Radial part 48 defines a center opening 50 communicating with, or analogously understood to form a part of, device passage 26. Radial part 48 extends radially outward from opening 50, and axial part 52 extends generally in an axial direction from radial part 48. As noted above, cap 22 may be rotationally fixed to valve body 14, meaning that cap 22 does not ordinarily rotate relative to valve body 14. Any of a wide variety of strategies could be used for coupling cap 22 to valve body 14 in this general manner. In one practical implementation strategy, as shown in FIG. 2 cap 22 may be equipped with one or more projections 54 that are received within mating indentations 56 in valve body 14. Cap 22 may have a roughly cylindrical, or hex-shaped configuration. Accordingly, one can readily visualize multiple different projections 54 spaced about an inside diameter of axial part 52, and received in corresponding indentations 56 in valve body 14, which may have a generally cylindrical configuration at least in the region received within cap 22. An inside diameter of axial part 52 might also have a non-cylindrical shape mating with an outer shape of valve body 14, to analogously couple the parts together in a manner in which rotation is limited.

Also shown in FIG. 2 is first valve 28 in cross section, and showing opening 30 communicating between a proximal surface 58 of valve 28, and a distal surface of valve 28. In the illustrated embodiment, proximal surface 58 may be substantially planar, whereas distal surface 60 may have a generally planar outer section and a generally planar inner section which are joined by a frustoconical section. In three dimensions, first valve 58 might have the form generally of a cylinder with a distally located axially projecting frustoconical shape extending from the cylinder. Also in the illustrated embodiment, opening 30 is shown as it might appear where configured as a slit, in other words an essentially two-dimensional cut extending all the way axially through first valve 28, but not extending radially all the way through. In alternative embodiments, a tricuspid valve configuration, or still another valve configuration such as multiple intersecting slits might be used. It is of course desirable that whatever configuration and materials are used for first valve 28 that it be capable of self-closing to at least provide the lower pressure fluid seal about a medical device passed through device passage 26, and also typically forming a lower pressure seal with itself when no device passes through.

As discussed above, cap 22 may be coupled to proximal body end 18 and connector 24 may be coupled to distal body end 20, of valve body 14. Proximal body end 18 may have a proximal end surface 63 which is shaped complementarily to a shape of first valve 28, and in particular a shape of surface 60. This general feature will enable first valve 28 to be seated upon valve body 14, and substantially seal against valve body 14 such that fluid does not leak out of mechanism 10 between first valve 28 and valve body 14, in a proximal direction. In FIG. 2, some minor clearances appear between first valve 28 and valve body 14 as well as cap 22. In a practical implementation strategy, the components of mechanism 10 will typically be sized and shaped such that very little, if any such clearances would exist, however they appear in the attached drawings for purposes of illustration. Valve body 14 further includes an outer body surface 62 extending from proximal body end 18 to distal body end 20, and an inner body surface 64 extending from proximal end surface 63 to a distal end surface 67. Inner body surface 64 defines a portion or segment of device passage 26. It may be noted that an inside profile of valve body 14 can be understood to define a largest inner diameter dimension at body end 18, a medium inner diameter dimension at body end 20, and a small inner diameter dimension between body ends 18 and 20. In a practical implementation strategy, valve body 14 may be formed with an inward protrusion 65 that defines a portion or segment of device passage 26, and each of first valve 28 and second valve 32 may be in contact with inward protrusion 65. A shape of inward protrusion 65 could be considered frustoconical where protrusion 65 faces and contacts first valve 28, planar and annular where protrusion 65 faces and contacts second valve 32, and cylindrical between valve 28 and valve 32. Inward protrusion 65 can broadly be understood to have an annular configuration, forming a restriction in the diameter of passage 26, and providing surfaces against which valves 28 and 32 seat.

As discussed above, connector 24 may be rotatable relative to valve body 14. In the illustrated embodiment, connector 24 is rotatably coupled with valve body 14 via mating of threads. Mechanism 10 may include a first thread 66 located upon valve body 14, and a second thread 68 mated with first thread 66 and located upon connector 24 such that rotation of connector 24 relative valve body 14 adjusts the axial location of connector 24 via mating engagement between first thread 66 and second thread 68. In the state depicted in FIG. 2, mechanism 10 is shown as it might appear where second valve 32 has not been axially compressed to form a second seal. It will be understood that rotating connector 24 relative to valve body 14 will via the engagement of threads 66 and 68 adjust an axial location of connector 24 relative to valve body 14. In other words, despite the fact that connector 24 may be attached to valve body 14, it can still be understood to have an adjustable axial location. In this vein, it can be noted that surface 67 is spaced an axial distance from an opposing surface 69 of connector 24. In the state depicted in FIG. 2, mechanism 10 is shown as it might appear where second valve 32 is not subjected to any axial compression, or not substantially so. Depending upon a direction of relative rotation of connector 24 relative valve body 14, the axial clearance between surfaces 67 and 69 could be expected to decrease as valve 32 is axially compressed, or increase as the state of axial compression of valve 32 is reduced.

Surface 69 may have a generally flat and annular configuration, and extends circumferentially around an axial projection 74 defining a portion or segment of passage 26, and extending toward valve 32. Projection 74 may be substantially cylindrical and extends circumferentially around axis 16, and has a set of concentric edges 76 that contact second valve 32. While other strategies for contacting second valve 32 to axially compress the same might be employed, the use of edges 76 is expected to assist projection 74 in gripping valve 32 during use. In the illustrated embodiment, projection 74 extends in a proximal direction from surface 69 and is part of connector 24. In alternative versions a similar projection might be part of valve body 14, and extend in a distal direction to contact a proximal side of valve 32, essentially reversing the configuration shown in FIG. 2. Valve 32 may actually seat between radially inner and radially outer edges 76. Given the self-opening bias of valve 32, relative rotation between connector 24 and valve body 14 to axially compress valve 32 will tend to radially deform valve 32 inwardly into contact with a medical device passed through passage 26, and such rotation will occur in opposition to the self-opening bias. Valve 32 could also be closed to form a range of fluid seals without a medical device passing through it, and the seal being formed by contact of the material of valve 32 with itself as opening 34 is closed.

Figure 3:
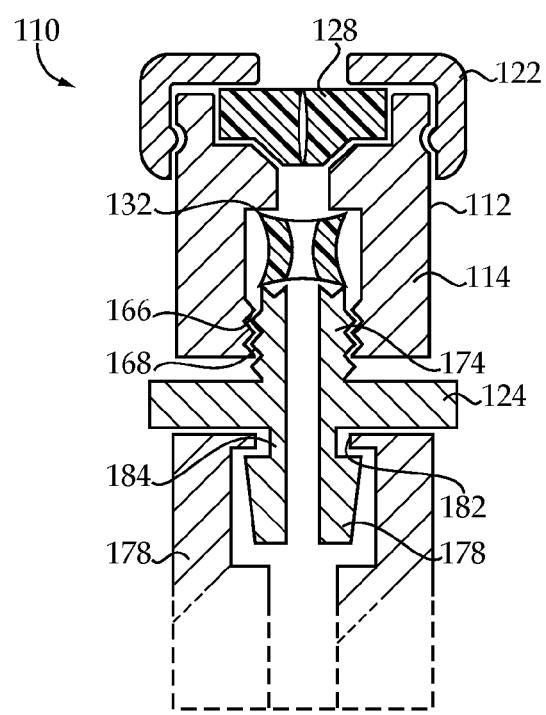
FIG. 3 is a sectioned side diagrammatic view of a part of a hemostasis mechanism, according to another embodiment.

Referring now to FIG. 3, there is shown a hemostasis mechanism 110 according to another embodiment, and including a housing 112 having a valve body 114, a cap 122, and a connector 124. Mechanism 110 functions in a manner generally analogous to that of mechanism 10 discussed above, but having certain differences, notably respecting the manner in which connector 124 is coupled with valve body 114. In the illustrated embodiment, connector 124 includes an external thread 168 mated with an internal thread 166 of valve body 114. External thread 168 is formed on an axial projection 174 of connector 124, and otherwise being generally analogous to projection 74 discussed above in its function of controlling a state of axial compression of a normally open valve 132. Mechanism 110 is also equipped with a normally closed valve 128, generally analogous to valve 28 discussed above. As in mechanism 10, projection 174 defines a portion of a device passage extending through housing 112, and extends circumferentially around a longitudinal axis, and extends axially into valve body 114 to contact second valve 132. Connector 124 is also equipped with a distal fitting 178, shown snap fitted through an opening 182 formed in an attached component 180 such as another housing piece of mechanism 110, or some other tubular body. A relatively narrow neck 184 of connector 124 is received within opening 182 when the components are coupled together as shown in FIG. 3. It will also be understood that rotation of connector 124 relative to valve body 114 also rotates connector 124 relative to component 180. While mechanism 110 may find application similar to those of mechanism 10, in certain instances allowing for relative rotation of connector 124 relative to an attached or coupled additional component such as component 180 will be considered advantageous.

INDUSTRIAL APPLICABILITY

Figure 4:
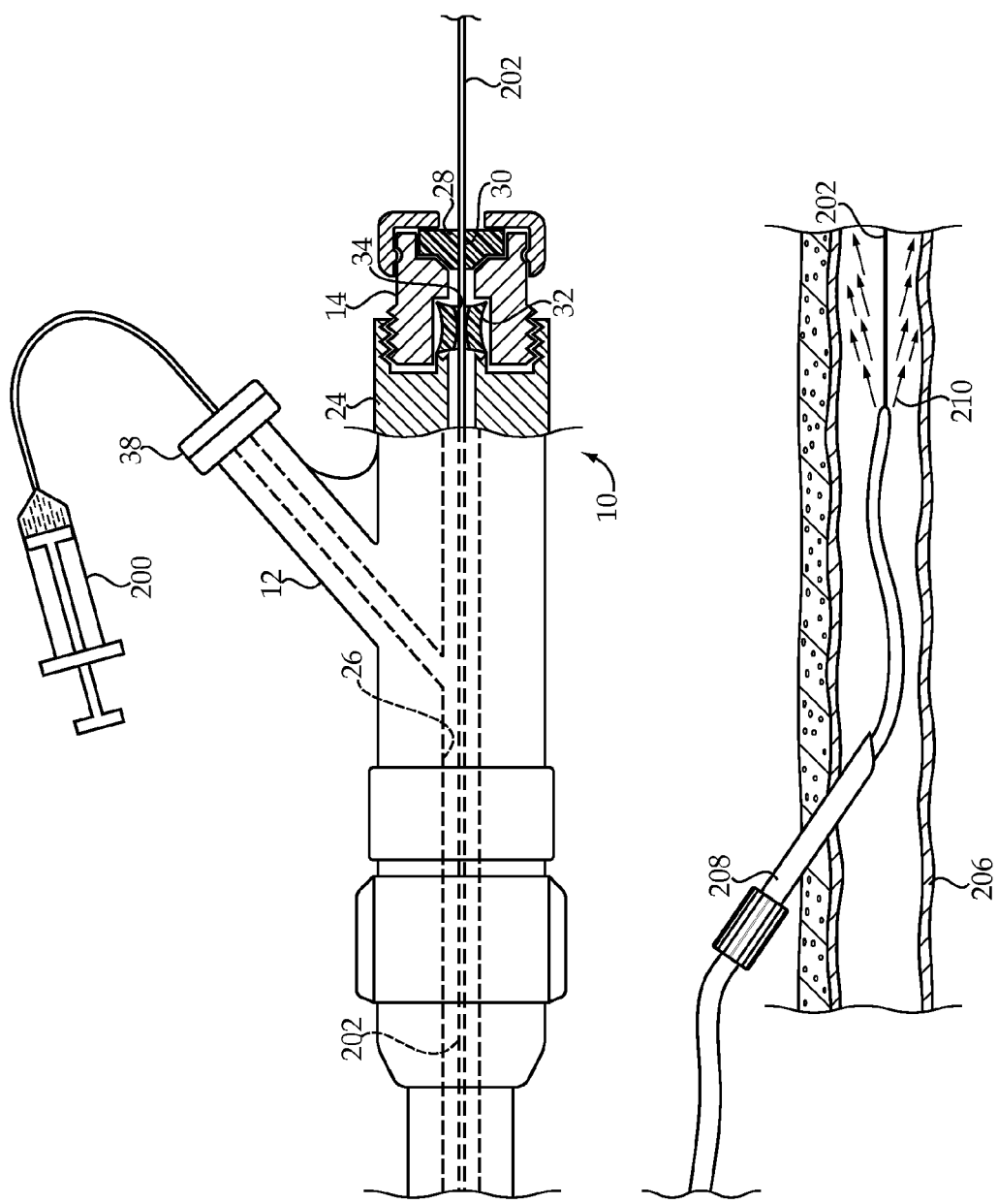
FIG. 4 is a partially sectioned side diagrammatic view of the hemostasis mechanism of FIG. 1 at one stage of percutaneously treating a patient, according to one embodiment.

Referring to the Figures generally, but in particular now to FIG. 4, there is shown mechanism 10 as it might appear at one stage of a treatment procedure according to the present disclosure. As noted above, mechanism 10, and mechanism 110, may be used to limit backflow of fluid during percutaneous transluminal treatment of a patient. Mechanism 10 is shown connected with a source of pressurized fluid for injection such as a syringe 200 coupled to fitting 38. Syringe 200 may be used to inject a fluid into device passage 26, thenceforth through a catheter 204 coupled with mechanism 10 and passing through an introducer 208 into a body lumen in a vessel 206 of a patient. Catheter 204 has been guided into vessel 206 via a wire guide 202. It will be recalled that valve 28 may have a self-closing bias, and normally closed opening 30 may be opened via pushing a medical device such as wire guide 202 through opening 30, deforming valve 28 radially outwardly in opposition to its self-closing bias. Valve 28 will tend to form a lower pressure seal about the medical device. Accordingly, in FIG. 4 wire guide 202 has been pushed through opening 30 in valve 28, and advanced through normally open opening 34 in valve 32. Valve 28 has thus formed a lower pressure seal about wire guide 202. A state of axial compression of valve 32 has been increased in opposition to its self-opening bias, and valve 32 has formed a higher pressure seal about wire guide 202 via deformation induced by the increase in the state of axial compression. Depending upon the point in the procedure which is being considered, one or both of valves 28 and 32 will block backflow of fluid of mechanism 10 by way of the corresponding fluid seal formed with wire guide 202.

In one practical implementation strategy, wire guide 204 might be advanced through mechanism 10 and into a body lumen of vessel 206, such as the lumen of a vein or artery, prior to the formation of the higher pressure seal with valve 32. In such a case, once fluid communication between mechanism 10 and the body lumen is established, blood may flow back through an introducer or the like into mechanism 10. The lower pressure seal formed via valve 28 can block backflow of blood through mechanism 10 in this general manner. Where it is desirable to inject a fluid from syringe 200, connector 24 may be rotated relative to valve body 14, to increase a state of axial compression of valve 32, squeezing valve 32 between valve body 14 and connector 24 such that valve 32 deforms radially inwardly into circumferential contact with catheter 204. As discussed above, this can occur by way of engaging mating threads on valve body 14 and connector 24. In the case of mechanism 10, it would be common for valve body 14 to be rotated by a clinician while connector 24 is held steady. Where mechanism 110 is used, it might be more common for connector 124 to be rotated while valve body 114 is held steady. In any event, the higher pressure seal formed by valve 32 can block backflow of the fluid injected via syringe 200, or another delivery device, which will typically be at a higher injection pressure than a pressure of blood that may find its way upstream into mechanism 10 and be blocked via valve 28.

Those skilled in the art will be familiar with the necessity to close and open valves in a hemostasis mechanism potentially numerous times during the course of a procedure. In some instances, a medical device can be initially placed within the patient via advancing it through the hemostasis mechanism, and then repositioned or advanced further, for various purposes. As the medical device is advanced, stopped, advanced again, etc., it generally remains desirable to prevent backflow of fluid whether it be blood, contrast, saline or another fluid. In certain known devices, it is necessary to manually manipulate a valve each time the medical device is repositioned within the patient. Alternatively, some hemostasis devices employing automatically closing or self-sealing valves do not require manual manipulation, but tend to squeeze about a medical device relatively tightly thus rendering the force required to push or pull the medical device through the valve relatively high.

In the present instance, mechanisms 10 and 110 provide a first valve which is relatively easy to push the medical device through, but which forms a seal that is suitably tight for various purposes, and particularly purposes connected with preparation for further treatment or analysis of the patient. Another way to understand this feature, is that valves 28 and 128 may provide relatively little resistance to sliding a medical device therethrough, but provide a sufficiently reliable seal that substantial bleedback through the corresponding mechanisms does not occur during initial placement of a medical device within the patient. Valves 32 and 132 can be employed to provide a substantially more robust fluid seal that can resist higher pressure injections or other conditions where the passive, self-closing seals would be overcome. The present disclosure also enables such flexibility and features in a relatively compact and simple design, having relatively few parts. Valves 28, 128 and 32, 132 also operate totally independently of one another, and are maintained at a fixed axial distance from one another within housing 12, such that neither valve needs to participate in operation of the other.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A hemostasis mechanism comprising:
a housing including a valve body defining a longitudinal axis extending between a proximal body end and a distal body end, and including a cap coupled to the proximal body end and having a fixed axial location along the longitudinal axis relative the valve body, a connector coupled to the distal body end and having an adjustable axial location along the longitudinal axis relative the valve body, and a device passage formed in part in each of the valve body, cap, and connector;
a first valve positioned at least partially within the device passage and having a fixed state of axial compression between the valve body and the cap, the first valve having a first opening formed therein and a self-closing bias such that the first opening is normally closed, and further forming a lower pressure seal about a medical device in response to pushing the medical device through the first opening in opposition to the self-closing bias; and
a second valve positioned within, and in contact with, the valve body, and the second valve having a range of states of axial compression along the longitudinal axis between the valve body and the connector, the second valve having a second opening formed therein and a self-opening bias such that the second opening is normally open, and further forming a higher pressure seal about the medical device via an adjustment of the state of axial compression in response to changing the axial location along the longitudinal axis of the connector in opposition to the self-opening bias.

2. The hemostasis mechanism of claim 1 wherein the first and second valves are in contact with the valve body upon opposite axial sides thereof, and positioned at a fixed axial distance along the longitudinal axis from one another within the housing.

3. The hemostasis mechanism of claim 2 wherein the valve body further includes an inward protrusion defining a portion of the device passage, and each of the first and second valves are in contact with the inward protrusion.

4. The hemostasis mechanism of claim 3 wherein the inward protrusion has an annular configuration.

5. A hemostasis mechanism comprising:
a housing including a valve body defining a longitudinal axis extending between a proximal body end and a distal body end, and including a cap coupled to the proximal body end and having a fixed axial location relative the valve body, a connector coupled to the distal body end and having an adjustable axial location relative the valve body, and a device passage formed in part in each of the valve body, cap, and connector;
a first valve positioned at least partially within the device passage and having a fixed state of axial compression between the valve body and the cap, the first valve having a first opening formed therein and a self-closing bias such that the first opening is normally closed, and further forming a lower pressure seal about a medical device in response to pushing the medical device through the first opening in opposition to the self-closing bias; and
a second valve positioned within, and in contact with, the valve body, and the second valve having a range of states of axial compression between the valve body and the connector, the second valve having a second opening formed therein and a self-opening bias such that the second opening is normally open, and further forming a higher pressure seal about the medical device via an adjustment of the state of axial compression in response to changing the axial location of the connector in opposition to the self-opening bias;
wherein the first and second valves are in contact with the valve body upon opposite axial sides thereof, and positioned at a fixed axial distance from one another within the housing; and
a first thread located upon the valve body, and a second thread mated with the first thread and located upon the connector such that rotation of the connector relative the valve body adjusts the axial location of the connector via mating engagement between the first and second threads.

6. The hemostasis mechanism of claim 5 wherein the connector further includes an axial projection along the longitudinal axis extending into the valve body and contacting the second valve.

7. The hemostasis mechanism of claim 6 wherein the axial projection defines another portion of the device passage and extends circumferentially around the longitudinal axis.

8. The hemostasis mechanism of claim 6 wherein the first thread includes an external thread and the second thread includes an internal thread.

9. The hemostasis mechanism of claim 6 wherein the first thread includes an internal thread and the second thread includes an external thread.

10. A method of limiting backflow of fluid during percutaneous transluminal treatment of a patient using a hemostasis mechanism that includes a housing including a valve body defining a longitudinal axis extending between a proximal body end and a distal body end, and including a cap coupled to the proximal body end and having a fixed axial location along the longitudinal axis relative the valve body, a connector coupled to the distal body end and having an adjustable axial location along the longitudinal axis relative the valve body, and a device passage formed in part in each of the valve body, cap, and connector; a first valve positioned at least partially within the device passage and having a fixed state of axial compression between the valve body and the cap, the first valve having a first opening formed therein and a self-closing bias such that the first opening is normally closed, and further forming a lower pressure seal about a medical device in response to pushing the medical device through the first opening in opposition to the self-closing bias; and a second valve positioned within, and in contact with, the valve body, and the second valve having a range of states of axial compression along the longitudinal axis between the valve body and the connector, the second valve having a second opening formed therein and a self-opening bias such that the second opening is normally open, and further forming a higher pressure seal about the medical device via an adjustment of the state of axial compression along the longitudinal axis in response to changing the axial location of the connector in opposition to the self-opening bias, and the method comprising the steps of:
pushing a medical device for introducing into the patient through the normally closed first opening in the first valve having the fixed state of axial compression between the valve body and the cap in the hemostasis mechanism;
forming the lower pressure seal about the medical device via the self-closing bias of the first valve;
advancing the medical device through the normally open second opening in the second valve having the range of states of axial compression between the valve body and the connector in the hemostasis mechanism;
increasing the state of axial compression of the second valve in opposition to the self-opening bias thereof;
forming the higher pressure seal about the medical device via deformation of the second valve induced by the increase in the state of axial compression; and
blocking backflow of fluid through the hemostasis mechanism via at least one of the higher pressure and lower pressure seals.

11. The method of claim 10 further comprising a step of advancing the medical device into a body lumen of the patient prior to the formation of the higher pressure seal, and wherein the step of blocking includes blocking backflow of blood through the hemostasis mechanism via the lower pressure seal.

12. The method of claim 11 further comprising a step of injecting fluid through the hemostasis mechanism into the body lumen, and wherein the step of blocking includes blocking backflow of fluid induced via a pressure of the injection.

13. The method of claim 10 wherein the step of increasing further includes squeezing the second valve between the valve body and the connector such that the second valve deforms radially inwardly into circumferential contact with the medical device.

14. The method of claim 13 wherein the step of increasing further includes engaging mating threads on the valve body and the connector via rotating the connector relative the valve body.

15. The method of claim 14 wherein rotating the connector includes rotating the connector relative to a tubular body piece coupled to the connector opposite the valve body.

16. The method of claim 14 wherein engaging mating threads includes engaging an internal thread on the valve body with an external thread on the connector.

17. The method of claim 16 wherein engaging mating threads includes engaging an external thread on the valve body with an internal thread on the connector.

18. The method of claim 13 wherein squeezing the second valve further includes squeezing the second valve between the connector and an inward protrusion on the valve body defining a portion of a device passage extending through the hemostasis mechanism.

* * * * *